(12) United States Patent
Sergeant et al.

(10) Patent No.: US 9,759,728 B2
(45) Date of Patent: Sep. 12, 2017

(54) METHODS FOR DETERMINING HUMAN SPERM QUALITY

(71) Applicants: INSERM (INSTITUT NATIONAL DE LA SANTÉ ET DE LA RECHERCHE MÉDICALE, Paris (FR); UNIVERSITÉ DE DROIT ET DE LA SANTÉ DE LILLE 2, Lille (FR); CENTRE HOSPITALIER REGIONAL UNIVERSITAIRE DE LILLE, Lille (FR)

(72) Inventors: Nicolas Sergeant, Lille (FR); Valerie Mitchell, Lille (FR); Fanny Jumeau, Rouen (FR); Julien Sigala, Lille (FR)

(73) Assignees: Institut National de la Sante et de la Recherche Medicale (INSERM), Paris (FR); Universite de Droit et de la Sante de Lille 2, Lille (FR); Centre Hospitalier Regional Universitaire de Lille, Lille (FR)

( * ) Notice: Subject to any disclaimer, the term of this patent is extended or adjusted under 35 U.S.C. 154(b) by 0 days.

(21) Appl. No.: 14/913,856

(22) PCT Filed: Sep. 4, 2014

(86) PCT No.: PCT/EP2014/068783
§ 371 (c)(1),
(2) Date: Feb. 23, 2016

(87) PCT Pub. No.: WO2015/032842
PCT Pub. Date: Mar. 12, 2015

(65) Prior Publication Data
US 2016/0356785 A1 Dec. 8, 2016

(30) Foreign Application Priority Data
Sep. 5, 2013 (EP) .................... 13306212

(51) Int. Cl.
| | | |
|---|---|---|
| C12Q 1/00 | (2006.01) | |
| C12Q 1/48 | (2006.01) | |
| C12N 9/00 | (2006.01) | |
| C12N 9/12 | (2006.01) | |
| G01N 33/559 | (2006.01) | |
| C07K 1/00 | (2006.01) | |
| G01N 33/68 | (2006.01) | |

(52) U.S. Cl.
CPC . *G01N 33/689* (2013.01); *G01N 2333/91215* (2013.01)

(58) Field of Classification Search
CPC .................. G01N 2333/91215; G01N 33/689
USPC ........ 435/4, 15, 183, 194; 204/456; 530/350
See application file for complete search history.

(56) References Cited

U.S. PATENT DOCUMENTS 5,569,581 A * 10/1996 Killian ................ G01N 33/689
424/520

OTHER PUBLICATIONS

Al-Somai et al., Low molecular weight components in bovine semen diffusate and their effects on motility of bull sperm. Reprod. Fertil. Dev., 1994, vol. 6: 165-171.*
Luconi et al., Role of a-kinase anchoring proteins (AKAPs) in reproduction. Frontiers in Biosci., 2011, vol. 16: 1315-1330.*
Mandal et al., Deficiency in major high-molecular weight seminal proteins in men producing poorly coagulating and alkaline liquid ejaculates. Int. J. Androl., 1992, vol. 15: 308-319.*
Eddy et al, "Fibrous sheath of mammalian spermatozoa", Microscopy Research and Technique, May 1, 2003, pp. 103-115, vol. 61, No. 1.
Carrera et al., "Regulation of protein tyrosine phosphorylation in human sperm by a calcium/calmodulin-dependent mechanism: identification of A kinase anchor proteins as major substrates for tyrosine phosphorylation", Developmental Biology, Nov. 25, 1996, pp. 284-296, vol. 180, No. 1.

* cited by examiner

*Primary Examiner* — Ganapathirama Raghu
(74) *Attorney, Agent, or Firm* — Whitham Curtis & Cook, PC

(57) ABSTRACT

The present invention relates generally to the fields of reproductive medicine. More specifically, the present invention relates to methods and kits for determining the human sperm quality.

10 Claims, 4 Drawing Sheets

METHODS FOR DETERMINING HUMAN SPERM QUALITY

FIELD OF THE INVENTION

Figure 1:
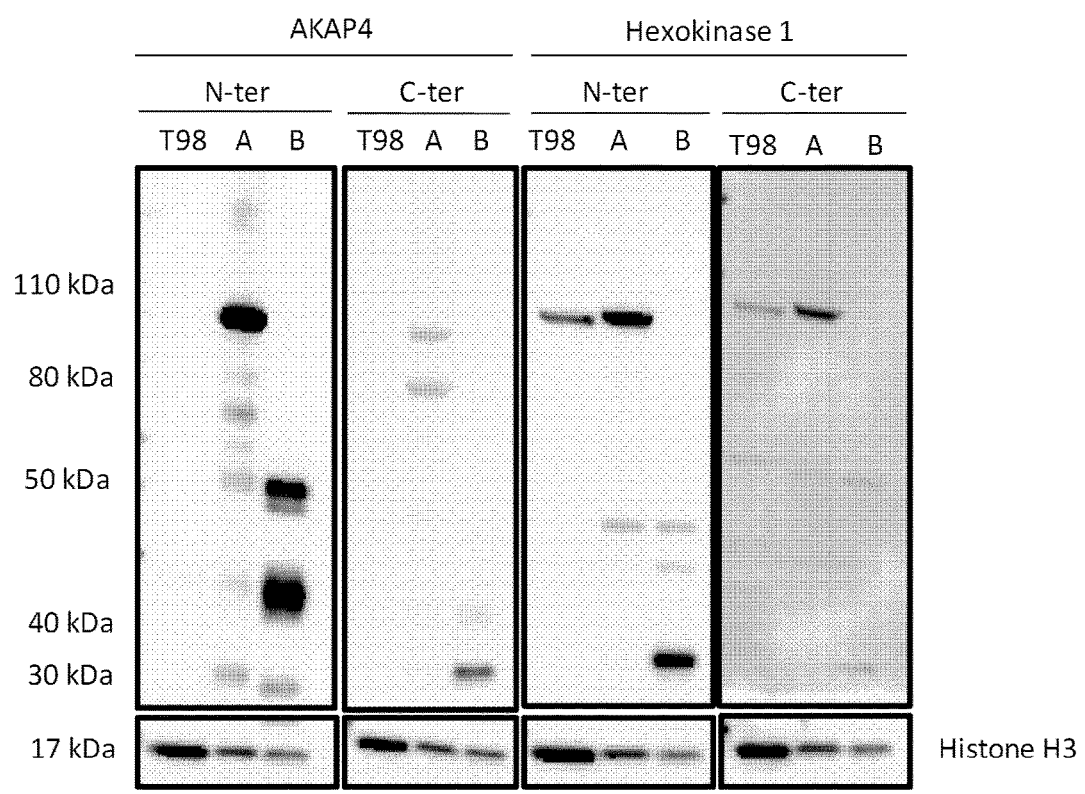

The present invention relates generally to the fields of reproductive medicine. More specifically, the present invention relates to methods and kits for determining the human sperm quality.

BACKGROUND OF THE INVENTION

Currently, 15% of couples present difficulties to conceive and one in seven men present alteration of sperm quality (Krausz 2011). The semen is constituted of a non-cellular phase, the seminal plasma, a complex fluid composed of prostatic and seminal vesicle secretions and a cellular phase containing spermatozoa. To evaluate the quality of the semen, a descriptive analysis is often performed. Essential sperm parameters are evaluated including the sperm concentration, the motility and the morphology of spermatozoa. The lower reference limits of these parameters are given according to the WHO criteria (2010). Motility, morphology and sperm count are considered as markers of fertility and used to predict pregnancy success (Aitken 2006). Despite having apparently normal sperm parameters, the origin of men infertility remains unknown for 50% of individuals classified as having a normozoospermia (Krausz 2011). Thus, fertilization failure are yet observed and remains ill-defined (Krausz 2011). With this in mind, descriptive analyses of the semen show limits to predict fertility and new tools are certainly needed to understand sperm physiology and define a new approach to identify the origins of men fertilization failure as well as to help couples orientation to current assisted reproduction technologies (ART).

Spermatozoa should be considered to define the fertility index. Spermatozoa are highly differentiated cells. During spermatogenesis, they progressively lose their cellular organelles with the cytoplasmic droplet and became motile and able to fertilize during their maturation in the epididymis and in female genital tractus. Hereby, there is no or weak protein synthesis in a mature spermatozoa. However, spermatozoa cell and its environment (epididymis, male and female genital tractus) interact and might consequently modifying the spermatozoa proteome (Plessis et al. 2011). Currently, recent advances in proteomic technology have produced valuable tools for studying sperm proteins. Proteins studied and proposed as potential fertility marker are mostly revealed through their fertility functions. First, due to crucial role of the sperm nucleus, the ratio protamine 1 (P1)/protamine 2 (P2) is widely studied and P1/P2 ratio is correlated with fertilization ability (Aoki et al. 2006; Oliva 2006; de Mateo et al. 2007; de Mateo et al. 2009). De Mateo and collaborators demonstrated a negative correlation between prohibitin expression, a mitochondrial protein implied in sperm motility (Wang et al. 2012), and level of P1/P2 ratio (de Mateo et al. 2007). Acrosomal vesicle is required for spermatozoa penetration of the oocyte zona pellucida and acrosin expression is used as a marker of its integrity (Zahn et al. 2002); (Liu et al. 2008). Chaudhury et al. studied proacrosin/acrosin expression in men with normal sperm parameters but unexplained infertility. Proacrosin/acrosin system seems to be disturb in men with normal sperm parameters but unexplained infertility and proposed this protein as a marker (Chaudhury et al. 2005). More recently, Blomberg Jensen and collaborators (Blomberg Jensen et al. 2012), proposed for the first time vitamin D metabolizing enzyme CYP24A1 expressed in the annulus of spermatozoa as a novel marker of semen quality. Sperm membrane is a fundamental actor in fertility and its composition can be disturb by several factors such as oxygen reactive species of thus induce the dysfunction of spermatozoa fertility (Glander et al. 2002; Aitken 2006; Cocuzza et al. 2007; Bresler et al. 2011; Aitken 2011). Yet, many alterations of sperm proteome may contribute to male infertility and those factors remain ill-defined.

SUMMARY OF THE INVENTION

The present invention relates to methods and kits for determining the human sperm quality.

DETAILED DESCRIPTION OF THE INVENTION

The inventors have evaluated the proteome quality of human spermatozoa and its relationship with the sperm parameters. The inventors hypothesized that assessment of proteome quality profile could be related to semen parameters in order to potentially discriminate between subclasses of normozoospermia and determination of infertility risk factor. To address this issue, the inventors have studied the semen obtained from a cohort of 161 men with normal semen parameters. Spermatozoa were isolated from seminal plasma using a one-step density gradient, a sperm cell isolation method adapted from the method routinely used in clinic but herein adapted for the analysis of the whole spermatozoa proteome. Sperm proteins were extracted and analyzed by 1D SDS-PAGE and protein staining and markers were assessed by immunoblotting. Spermatozoa Proteome Quality Index (SPQI) of the 1D-electrophoresis profile was established and analyzed in relationship with sperm parameters. Moreover, on a follow-up study, the inventors have analyzed the birth success rate observed among men having SPQI belonging to the two groups defined. Together, our data demonstrated that SPQI is useful to discriminate between two groups of mens among which one may have a lower fertility and should be orientated to assisted reproduction technologies.

The inventor's protocol of sperm isolation preserves the morphology of spermatozoa. Analysis of markers from different sperm cell compartments showed that sperm proteins extraction were not selective toward cellular compartment and was consistent with the preservation of spermatozoa integrity. However, 1D Coomassie blue stained proteins showed altered expression of proteins characterized by mass spectrometry and demonstrated to correspond to AKAP4 and Hexokinase1. Immunoblotting of AKAP4 and Hexokinase1 using N- and C-terminal specific antibodies showed a proteolyzed profile of both proteins in many semen samples. Since, these proteins are major semen proteins, the Coomassie blue stain profiles from the 161 samples showed that these protein bands were diminished in almost 50% of individuals. The inventors defined two groups and established a spermatozoa proteome quality index (SPQI) following quantification of Coomassie stained bands corresponding to AKAP4 and Hexokinase 1. This SPQI was compared with the semen parameters and showed a significant lower sperm motility in SPQI group B. Moreover, preliminary data regarding the birth success rate after assisted reproduction technology strongly suggest a lower success of conceive for men belonging to the SPQI group B. Altogether, the inventor's results suggest that the global proteome analysis of human spermatozoa herein referred to as SPQI in parallel to the analysis of AKAP4 and Hexokinase1 may be a useful biomarker for the prognosis of sperm quality, sperm motility and could be useful to help the orientation of couples between the three current assisted reproduction technologies proposed to couples.

Accordingly, the present invention relates to a method for assessing sperm quality in an infertile or hypofertile subject or a subject with difficulty to conceive for more than one year, comprising a step of measuring in a semen sample obtained from said subject the expression level of at least one biomarker selected from AKAP4 and Hexokinase 1.

Typically, the expression level of one or two biomarkers is measured.

As used herein, the term "subject" denotes a mammal, such as a rodent, a bovine, an ovine, a feline, a canine, and a non-human primate. In a particular embodiment of the invention, a subject refers to any subject (preferably human) afflicted with male infertility or hypo fertility or difficulties to conceive within more than one year. In another particular embodiment of the invention, the subject is classified as a normozoospermic subject.

The term "sperm quality" refers to sperm and spermatozoa parameters and the ability of semen or spermatozoa to perform successfully fertilization leading to embryo development that is able to give rise to pregnancy. Essential sperm parameters include the sperm concentration, the motility and the morphology of spermatozoa. The lower reference limits of these parameters are given according to the WHO criteria (2010). Motility, morphology and sperm count are considered as markers of fertility and used to predict pregnancy success. The term "good sperm quality" refers to sperm or spermatozoa having normal parameters leading to high fertility rate. The term "bad sperm quality" refers to sperm or spermatozoa having abnormal parameters leading to low fertility rate or not leading to fertility. As used in the present invention, the term "sperm quality" also refers to infertility index, sperm proteome integrity, or spermatozoa proteome quality index (SPQI).

The term "normozoospermia" has its general meaning in the art and refers to a subject afflicted by male infertility associated with apparently normal sperm parameters in seminogram and in sperm morphology characterization (spermocytogram) (Krausz et al., 2011).

The term "AKAP4" has its general meaning in the art and refers to A-kinase anchor protein 4 having the accession number NP_003877 (isoform 1), NP_647450 (isoform 2). The term "AKAP4" refers to a structural protein identified in fibrous sheath and that binds cAMP-dependant-kinase (PKA) to initiate and mediate sperm motility (Brown 2002; Moretti et al. 2007). AKAP4 protein is encoded by a X-linked genes into a precursor: pro-AKAP4 (97 kDa) that cleaves in AKAP4 (82 kDa) (Turner et al. 1998; Eddy, Toshimori, and O'Brien 2003).

The term "Hexokiase 1" or "HK1" has its general meaning in the art and refers to Hexokiase 1, a predominant glycolytic enzyme presents in spermatozoa (Eddy, Toshimori, and O'Brien 2003; Nakamura et al. 2008) having the accession number NP_000179, including human isoforms NP277031, NP277032, NP277033, NP277035. Hexokinase 1 is mainly localized in fibrous sheath of spermatozoa and uses ATP to phosphorylate glucose to glucose-6-phosphate necessary for sperm motility.

As used herein the term "measuring" refers to measuring the expression level of the biomarkers of the invention. The term "measuring" as used herein also includes detecting the presence or absence of the biomarkers of the invention. The term "measuring" as used herein also refers to measuring the expression level of the full-length biomarkers of the invention. The term "measuring" as used herein also refers to measuring the proteolysis level of the biomarkers of the invention. A decrease of the expression level of the full-length biomarkers is indicative of biomarkers proteolysis.

The term "proteolysis" has its general meaning in the art and refers to protein cleavage and degradation. Proteolysis is known to be a physiological phenomenon in spermatozoa. Ubiquitin dependent proteolysis is one of most important pathways implied in spermatogenesis, sperm quality control and fertilization (Sutovsky 2003; Sutovsky 2011). Moreover, proteasome mediated proteolysis implied in acrosomal reaction and digestion of vitelline membrane (Zimmerman and Sutovsky 2009; Rawe et al. 2008; Kong, Diaz, and Morales 2009).

The method according to the present invention further comprises a step consisting of comparing the expression level of the AKAP4 and Hexokinase 1 measured in the semen sample with a reference value, wherein detecting differential in the expression of the biomarkers between the sample and the reference value is indicative of the sperm quality.

Typically, the reference value may correspond to the expression level of the biomarkers measured in the semen sample of a fertile subject. Accordingly higher or equal expression level of the biomarkers in the semen sample than the reference value is indicative for a good sperm quality, and accordingly, lower expression level of the biomarkers in the semen sample than the reference value is indicative for a bad sperm quality.

Alternatively, the reference value may correspond to the expression level of the biomarkers measured in the semen sample of an infertile or hypofertile subject. Accordingly, a higher expression level of the biomarkers in the semen sample than the reference value is indicative of a good sperm quality, and accordingly, a lower or equal expression level of the biomarkers in the semen sample than reference value is indicative of a bad sperm quality.

Typically, the absence of at least one biomarker indicates that the sperm of the subject has a bad quality.

In one embodiment, the present invention relates to a method for assessing sperm quality in an infertile or hypofertile subject or a subject with difficulty to conceive for more than one year, comprising a step of measuring in a semen sample obtained from said subject the proteolysis level of at least one biomarker selected from AKAP4 and Hexokinase 1.

The method according to the invention further comprises a step consisting of comparing the proteolysis level of the AKAP4 and Hexokinase 1 measured in the semen sample with a reference value, wherein detecting differential in the proteolysis level of the biomarkers between the sample and the reference value is indicative of the sperm quality.

Typically, the reference value may correspond to the proteolysis level of the biomarkers measured in the semen sample of a fertile subject. Accordingly, a higher proteolysis level of the biomarkers in the semen sample than the reference value is indicative for a bad sperm quality, and accordingly, a lower or equal proteolysis level of the biomarkers in the semen sample than the reference value is indicative for a good sperm quality.

Alternatively, the reference value may correspond to the proteolysis level of the biomarkers measured in the semen sample of an infertile or hypofertile subject. Accordingly, a higher or equal proteolysis level of the biomarkers in the semen sample than the reference value is indicative for a bad sperm quality, and accordingly, a lower proteolysis level of the biomarkers in the semen sample than the reference value is indicative for a good sperm quality.

In another particular embodiment, the present invention relates to a method for assessing sperm quality in an infertile or hypo fertile subject or a subject with difficulty to conceive for more than one year, comprising the steps of:
i) providing a semen sample from said subject,
ii) isolating spermatozoa from said semen sample,
iii) isolating spermatozoa proteins,
iv) analysing said proteins isolated in step iii) in a 1D SDS-PAGE and blue staining,
v) providing a numerical analysis of said blue stained gel of step iv),
vi) selecting protein bands between Low molecular weights 15 to 30 kDA and protein bands between High molecular weights 80 and 110 kDa,
vii) representing each band by a densitometric curve and calculating the area under curve,
viii) and calculating the ratio between the area under curve from Low molecular weights and High molecular weights band intensities.

In a particular embodiment, the Coomassie blue staining may be used.

The term "densitometric curve" refers to the curve representing protein band intensity signal.

Typically, a ratio calculated in step viii) of the present invention comprised between 1 and 2 is indicative of good sperm quality, and a ratio above 2 is indicative of a bad sperm quality.

In one embodiment, the steps i), ii) and iii) of the present invention may be performed according to the example detailed below. Accordingly, the semen is obtained after 3 and 5 days of sexual abstinence by masturbation and allowed to liquefy for 30 min at 37° C. After liquefaction, the semen parameters (volume, pH, cell counting and motility) are evaluated according to the WHO criteria 2010. The spermatozoa are separated from the round cells and the seminal plasma by a density gradient composed of 50% ferticult (Fertipro, Beernem, Belgium)/50% PureSperm (Nidacon, Mölndal, Sweden) in a 15 ml sterile Falcon tube (Falcon). After centrifugation (350×g, 20 min at room temperature), the sperm pellet is washed once with 1 mL of Tris buffer saline (TBS) (Tris-HCl 0.1 mM pH 7.6, 100 mM NaCl) by centrifugation (350×g, 20 min at room temperature). The sperm or spermatozoa protein extraction may be performed by resuspending the pellet in 500 µl of lysis buffer containing non-buffered 20 mM Tris, 2% SDS, 1% Nuclease Mix (Life Science GE Healthcare, Piscataway N.J. USA). The lysates are sonicated on ice (40 Hz, 60 pulses) and centrifuged (14,000×g, 20 min at 4° C.). The supernatants are recovered and pellets discarded. The protein concentrations are established according to the manufacturer's instructions (Bradford Assay, BioRad, Calif. USA). Protein lysates is frozen at −80° C. until the use in the method according to the invention.

The method of the invention is particularly suitable for predicting fertility, to identify the origins of men fertilization failure as well as to help couples orientation to current assisted reproduction technologies (ART). The method of the invention is particularly suitable for determining whether an assisted reproduction technology (ART) of the infertile or hypofertile or male subject with difficulty to conceive for more than one year shall be performed with a reasonable expectation of success. In case when the subject is diagnosed with a good sperm quality, a procedure of assisted reproduction technology (ART) consisting of intrauterine Insemination (IUI) or classical in vitro fertilization (cIVF) may be preferred, and accordingly, in case when the subject is diagnosed with a bad sperm quality, a procedure of intracytoplasmic sperm injection (ICSI) may be directly performed.

The term "Assisted reproductive technologies" or "ART" has its general meaning in the art and refers to methods used to achieve pregnancy by artificial or partially artificial means. Assisted reproductive technologies include but are not limited to classical in vitro fertilization (cIVF), intracytoplasmic sperm injection (ICSI), and intrauterine insemination (IUI).

The term "Intrauterine Insemination" or "IUI" refers to intrauterine injection of sperm or spermatozoa directly into a uterus.

The term "classical in vitro fertilization" or "cIVF" refers to a process by which oocytes are fertilized by sperm outside of the body, in vitro. cIVF is a major treatment in infertility when in vivo conception has failed.

The term "intracytoplasmic sperm injection" or "ICSI" refers to an in vitro fertilization procedure in which a single sperm is injected directly into an oocyte. This procedure is most commonly used to overcome male infertility factors, although it may also be used where oocytes cannot easily be penetrated by sperm, and occasionally as a method of in vitro fertilization.

The method of the invention is also particularly suitable for monitoring a treatment capable of restoring normal sperm quality. Typically, said treatment may be a normozoospermia treatment. The "normozoospermia treatment" relate to any type of normozoospermia therapy undergone by the normozoospermic subjects previously to collecting the normozoospermic semen samples, including gonadotropin, Human Chorionic Gonadotropin (HCG), Human Menopausal Gonadotropin (HMG) and bromocryptine.

The method of the invention can be applied for monitoring the sterilization treatment (e.g., drug compounds) of a male subject. For example, the effectiveness of an agent to affect the biomarkers expression (as herein after described) according to the invention can be monitored during treatments of subjects receiving sterilization treatments. The "sterilization treatment" relate to any type of sterilization therapy undergone by the male subjects, including pharmacological sterilization.

Methods for Determining the Expression Level of a Biomarker

Methods for measuring the expression level of a biomarker in a sample may be assessed by any of a wide variety of well-known methods from one of skill in the art for detecting expression of a protein including, but not limited to, direct methods like mass spectrometry-based quantification methods, protein microarray methods, enzyme immunoassay (EIA), radioimmunoassay (RIA), Western blot analysis, Mesoscale discovery (MSD), Luminex, ELISPOT and Enzyme Linked Immunoabsorbant Assay (ELISA).

Said direct analysis can be assessed by contacting the sample with a binding partner capable of selectively interacting with the biomarker present in the sample. The binding partner may be an antibody that may be polyclonal or monoclonal, preferably monoclonal (e.g., a isotope-label, element-label, radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin), or an antibody fragment (e.g., a single-chain antibody, an isolated antibody hypervariable domain, etc.) which binds specifically to the protein translated from the gene encoding for AKAP4 and Hexokinase 1. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce anti-biomarker, single chain antibodies. Antibodies useful in practicing the present invention also include anti-biomarker fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to biomarker. For example, phage display of antibodies may be used. In such a method, single-chain Fv (scFv) or Fab fragments are expressed on the surface of a suitable bacteriophage, e. g., M13. Briefly, spleen cells of a suitable host, e. g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e. g., bacteria, the phage displays the antibody fragment. Phage display of antibodies may also be provided by combinatorial methods known to those skilled in the art. Antibody fragments displayed by a phage may then be used as part of an immunoassay.

In another embodiment, the binding partner may be an aptamer. Aptamers are a class of molecule that represents an alternative to antibodies in term of molecular recognition. Aptamers are oligonucleotide sequences or chemically modified oligopeptide sequences with the property to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as E. coli Thioredoxin A, that are selected from combinatorial libraries by two hybrid methods (Colas et al., 1996).

The binding partners of the invention such as antibodies or aptamers, may be labelled with a detectable molecule or substance, such as an isotope, an element, a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as an isotope, an element, a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be produced with a specific isotope or a radioactive molecule by any method known in the art. For example radioactive molecules include but are not limited to radioactive atom for scintigraphic studies such as I123, I124, In111, Re186, Re188, specific isotopes include but are not limited to 13C, 15N, 126I, 79Br, 81Br.

The aforementioned assays generally involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidene fluoride; diazotized paper; nylon membranes; activated beads, magnetically responsive beads, silicon wafers.

In a particular embodiment, an ELISA method can be used, wherein the wells of a microtiter plate are coated with a set of antibodies which recognize said biomarkers. A sample containing or suspected of containing said biomarkers is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art such as Singulex, Quanterix, MSD, Bioscale, Cytof.

In one embodiment, an Enzyme-linked immunospot (ELISpot) method may be used. Typically, the sample is transferred to a plate which has been coated with the desired anti-biomarker capture antibodies. Revelation is carried out with biotinylated secondary Abs and standard colorimetric or fluorimetric detection methods such as streptavidin-alkaline phosphatase and NBT-BCIP and the spots counted.

In one embodiment, when multi-biomarker expression measurement is required, use of beads bearing binding partners of interest may be preferred. In a particular embodiment, the bead may be a cytometric bead for use in flow cytometry. Such beads may for example correspond to BD™ Cytometric Beads commercialized by BD Biosciences (San Jose, Calif.). Typically cytometric beads may be suitable for preparing a multiplexed bead assay. A multiplexed bead assay, such as, for example, the BD™ Cytometric Bead Array, is a series of spectrally discrete beads that can be used to capture and quantify soluble antigens. Typically, beads are labelled with one or more spectrally distinct fluorescent dyes, and detection is carried out using a multiplicity of photodetectors, one for each distinct dye to be detected. A number of methods of making and using sets of distinguishable beads have been described in the literature. These include beads distinguishable by size, wherein each size bead is coated with a different target-specific antibody (see e.g. Fulwyler and McHugh, 1990, Methods in Cell Biology 33:613-629), beads with two or more fluorescent dyes at varying concentrations, wherein the beads are identified by the levels of fluorescence dyes (see e.g. European Patent No. 0 126,450), and beads distinguishably labelled with two different dyes, wherein the beads are identified by separately measuring the fluorescence intensity of each of the dyes (see e.g. U.S. Pat. Nos. 4,499,052 and 4,717,655). Both one-dimensional and two-dimensional arrays for the simultaneous analysis of multiple antigens by flow cytometry are available commercially. Examples of one-dimensional arrays of singly dyed beads distinguishable by the level of fluorescence intensity include the BD™ Cytometric Bead Array (CBA) (BD Biosciences, San Jose, Calif.) and Cyto-Plex™ Flow Cytometry microspheres (Duke Scientific, Palo Alto, Calif.). An example of a two-dimensional array of beads distinguishable by a combination of fluorescence intensity (five levels) and size (two sizes) is the Quantum-Plex™ microspheres (Bangs Laboratories, Fisher, Ind.). An example of a two-dimensional array of doubly-dyed beads distinguishable by the levels of fluorescence of each of the two dyes is described in Fulton et al. (1997, Clinical Chemistry 43(9):1749-1756). The beads may be labelled with any fluorescent compound known in the art such as e.g. FITC (FL1), PE (FL2), fluorophores for use in the blue laser (e.g. PerCP, PE-Cy7, PE-Cy5, FL3 and APC or Cy5, FL4), fluorophores for use in the red, violet or UV laser (e.g. Pacific blue, pacific orange). In another particular embodiment, bead is a magnetic bead for use in magnetic separation. Magnetic beads are known to those of skill in the art. Typically, the magnetic bead is preferably made of a magnetic material selected from the group consisting of metals (e.g. ferrum, cobalt and nickel), an alloy thereof and an oxide thereof. In another particular embodiment, bead is bead that is dyed and magnetized.

In one embodiment, protein microarray methods may be used. Typically, at least one antibody or aptamer directed against the biomarker(s) is immobilized or grafted to an array(s), a solid or semi-solid surface(s). A sample containing or suspected of containing the biomarker(s) is then labelled with at least one isotope or one element or one fluorophore or one colorimetric tag that are not naturally contained in the tested sample. After a period of incubation of said sample with the array sufficient to allow the formation of antibody-antigen complexes, the array is then washed and dried. After all, quantifying said biomarkers may be achieved using any appropriate microarray scanner like fluorescence scanner, colorimetric scanner, SIMS (secondary ions mass spectrometry) scanner, maldi scanner, electromagnetic scanner or any technique allowing to quantify said labels. In another embodiment, the antibody or aptamer grafted on the array is labelled.

In one embodiment, a mass spectrometry-based quantification methods may be used. Mass spectrometry-based quantification methods may be performed using either labelled or unlabelled approaches (DeSouza and Siu, 2012). Mass spectrometry-based quantification methods may be performed using chemical labeling, metabolic labeling or proteolytic labeling. Mass spectrometry-based quantification methods may be performed using mass spectrometry label free quantification, LTQ Orbitrap Velos, LTQ-MS/MS, a quantification based on extracted ion chromatogram EIC (progenesis LC-MS, Liquid chromatography-mass spectrometry) and then profile alignment to determine differential expression of biomarkers.

In one embodiment, the sperm proteins including AKAP4 and Hexokinase 1 full-length or proteolyzed fragments of the said proteins are labelled with fluorophores such cyanine dyes. The fluorescently labelled sperm sample is then processed as for an ELISA. It is incubated in plate coated with an AKAP4 or Hexokinase specific antibody. After a period enabling the formation of the antibody-fluorescently labelled antigen complexes, the plate is washed to remove unbound moieties and the fluorescence is directly measured according to the fluorophore used to be coupled.

In one embodiment, ELISA sandwich specifically designed to measure the non-proteolysed full-length AKAP4 and Hexokinase 1 proteins may be used. The protocol is detailed below. The principle is a sandwich ELISA with a capturing antibody against the C-terminus and the second antibody is against the N-terminus. This sandwich ELISA gives the concentration of the full-length AKAP4 and Hexokinase 1 proteins. If, the AKAP4 and Hexokinase 1 are proteolysed the concentration determine with this sandwich ELISA drops.

Kits of the Invention

The invention also relates to a kit for performing the methods as above described, wherein said kit comprises means for measuring the expression level of at least one biomarker selected from the group consisting of AKAP4 and Hexokinase 1 that are indicative of sperm quality. In particular embodiment the kit comprises means for measuring the expression levels of AKAP4 and Hexokinase 1. Typically the kit may include an antibody, or a set of antibodies as above described. In a particular embodiment, the antibody or set of antibodies are labelled as above described. In a particular embodiment, the kit may include an antibody, or a set of antibodies specific of AKAP4 and Hexokinase 1 proteolytic fragments. The kit may also contain other suitably packaged reagents and materials needed for the particular detection protocol, including solid-phase matrices, if applicable, and standards.

The invention will be further illustrated by the following figures and examples. However, these examples and figures should not be interpreted in any way as limiting the scope of the present invention.

FIGURES

FIG. 1: AKAP4 and Hexokinase 1 expression revealed by immunoblotting.

15 µg of spermatozoa total protein lysates were loaded. Lane T98 is corresponding of T98 glioblastoma cell lysate. Lane A is representative of sperm sample with a quality index comprised between 1 and 2. Lane B is a spermatozoa sample with a quality index upper/over than 1 and 2. AKAP4 N-ter/C-ter, Hexokinase N-ter/C-ter and Histone H3 antibodies were used. The full-length AKAP4 protein is detected at an apparent MW of 95 kDa. The apparent MW of hexokinase 1 is of 100 kDa. Histone H3 were detected at apparent MW of 17 kDa and assessed that the same quantity of proteins were loaded.

Figure 2:
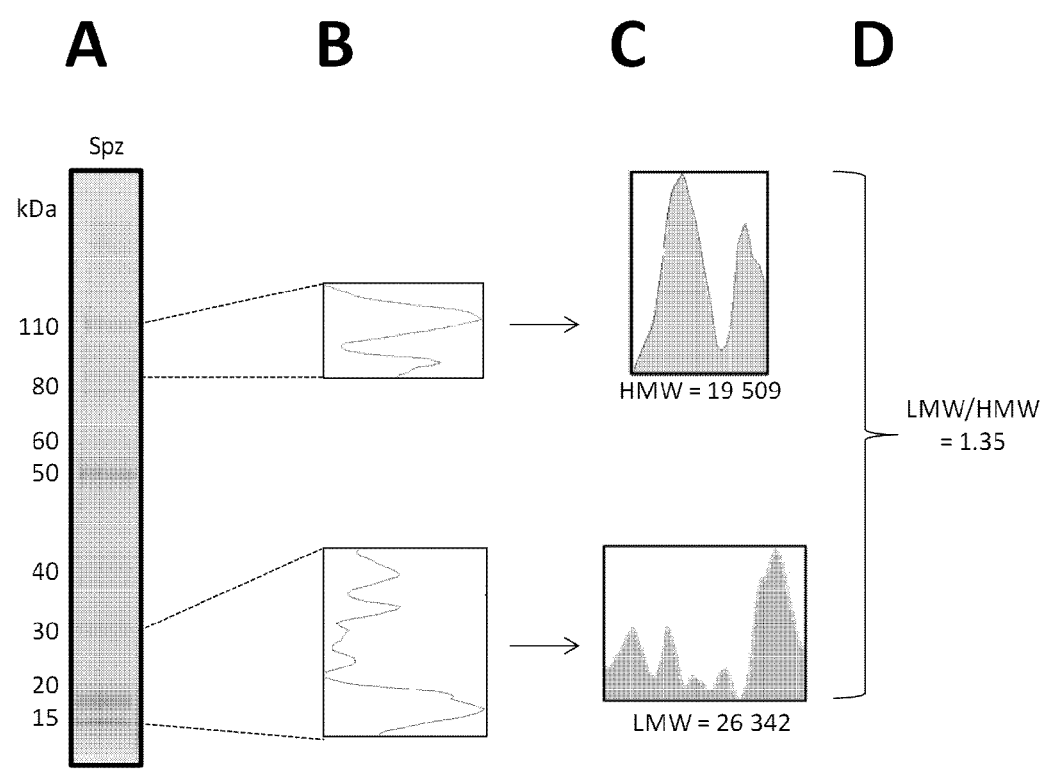

FIG. 2: Method to calculate SPQI

15 µg of spermatozoa proteins isolated from one ejaculate are loaded on a 1D SDS-Page and Coomassie stained (A). Picture from gel was analyzed. Background was eliminated. Windows from 15 to 30 kDa and 80 to 110 kDa were selected (B). Each bands were represented by a pic. Area under curve was calculated (C). Ratio LMW/HMW was established (D).

Figure 3A:
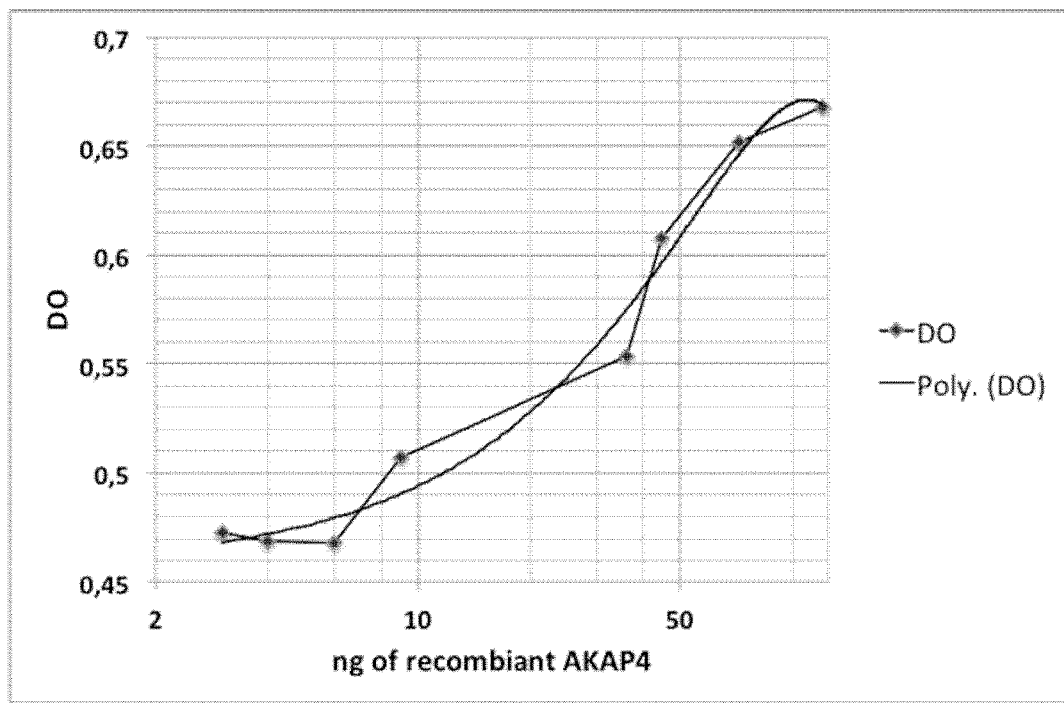
Figure 3B:
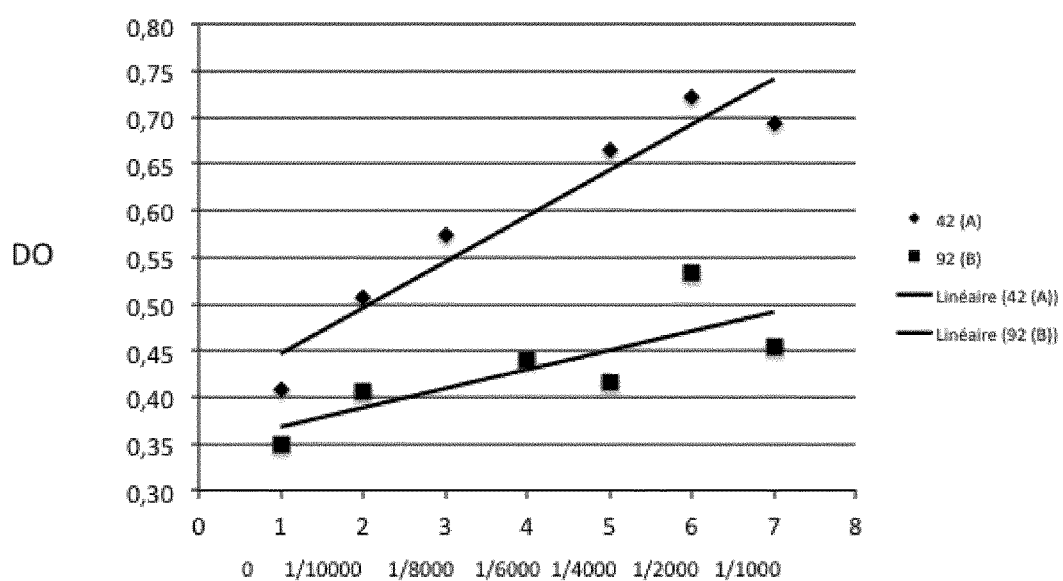

FIG. 3: Sandwich ELISA to measure the concentration of full-length AKAP4.

A. Growing concentration of recombinant human AKAP4 [AKAP4 (Human) Recombinant Protein (Q01) (Cat#:

H00008852-Q01)] from 0.1 ng to 120 ng were measured using the Sandwich AKAP4 ELISA. B. Serial dilutions of sperm samples from a subject of the index A group or the index B group were assayed. Note that at a dilution of 1/2000 AKAP4 concentration is measured in sample A42 but not in the B92. According to the standard curve, in subject A, the estimated concentration of full-length AKAP4 is above 120 ng at a dilution of 1/2000 whereas in subject B, the concentration is below 1 ng.

EXAMPLES

Example 1

Material & Methods

Semen and Semen Quality Assessment

Human semen samples were collected from anonymous men who attended the infertility department (Lille University center hospital). The semen were obtained between 3 and 5 days of sexual abstinence following masturbation and allowed to liquefy 30 min at 37° C. After liquefaction, the semen parameters (volume, pH, cell counting and motility) were evaluated according to the WHO criteria 2010. Spermatozoa were diluted (1/20) in Ringer medium and counted with an hemocytometer (Malassez cell counting). The progressive motility was evaluated by light microscopy on 5 fields and 100 spermatozoa were observed. The progressive motility (PR) is defined by the number of spermatozoa cells moving actively, either linearly or in a large circle, regardless of speed (World Health Organization 2010). The sperm morphology characterization (spermocytogram) was performed after Schorr's staining Only sperm above the lower references limits of all semen parameters were included in the present study. The local ethic committee on human subjects has approved the collection of semen samples. Men were given informed consent for the use of their semen for research purposes.

Follow-Up of Men in Assisted Reproductive Technology (ART)

Six months following the sperm analysis, couples remaining with difficulties to conceive were oriented to the Lille Hospital infertility department for reproductive assistance. Information was collected about the birth outcomes of ART pregnancies which had been performed in the infertility centre of the CHRU of Lille (Table 3).

Isolation of Spermatozoa

Sperm cells were separated from the semen plasma and round cells by a density gradient composed of 50% ferticult (Fertipro, Beernem, Belgium)/50% PureSperm (Nidacon, Mölndal, Sweden) in a 15 ml sterile Falcon tube (Falcon). After centrifugation (350×g, 20 min at room temperature), the sperm pellet was washed once with 1 mL of Tris buffer saline (TBS) (Tris-HCl 0.1 mM pH 7.6, 100 mM NaCl) by centrifugation (350×g, 20 min at room temperature).

Sperm Protein Extracts

The pellet was resuspended in 500 µl of lysis buffer containing non-buffered 20 mM Tris, 2% SDS, 1% Nuclease Mix (Life Science GE Healthcare, Piscataway N.J. USA). The lysates were sonicated on ice (40 Hz, 60 pulses) and centrifuged (14,000×g, 20 min at 4° C.). The supernatants were recovered and pellets were discarded. The protein concentrations were established according to the manufacturer's instructions (Bradford Assay, BioRad, Calif. USA). Protein lysates were frozen at −80° C. until used. Proteins from a cell lineage of human glioblastoma (T98) were extracted following the same procedure as for spermatozoa and was used in parallel of sperm protein to assess the antibody labeling by western blotting.

SDS-PAGE of Sperm Proteins

A total of 15 µg of sperm or T98 cell protein extracts was diluted in LDS 2× (Lithium dodecyl sulfate, Invitrogen) according to the manufacturer's instructions. Protein homogenates were heated at 100° C. during 10 min, quickly spun at 500×g using a bench centrifuge and loaded on 4-12% acrylamide gel (NuPage® Bis-Tris PreCast 12 wells, Life Technologies, Carlsbad Calif. USA). Molecular weight markers (Novex and Magic Marks, Life Technologies) were loaded in the first well. Electrophoresis was performed under a continuous potential of 200V during 1 h. Polyacrylamide gel was stained with Coomassie Blue [0.1% Blue G250 (Biorad, Calif. USA), 50% ethanol (v/v), 10% acetic acid (v/v) and $H_2O$]. Protein staining was visualized after washing with a destaining solution containing 7% (v/v) of acetic acid, 10% ethanol in $H_2O$. The gel was digitized with an Epson perfection V750 Pro scanner (Epson, France) and acquired using Adobe Photoshop Element 9 Software (Adobe, France). Images were analyzed using ImageJ software version 1.47c (NIH). ImageJ numerical treatment only included noise background reduction without modifying the original digitized image.

NanoLC-MALDI-TOF-MS/MS Experiments

Following tryptic digestion of Coomassie blue stained protein bands, nanoseparation was performed on an U3000 nano-HPLC system (Dionex-LC-Packings, Sunnyvale, Calif., USA). After a pre-concentration step (C18 cartridge, 300 µm, 1 mm), peptide samples were separated using a Pepmap C18 column (75 µm, 15 cm) by applying an acetonitrile/0.1% TFA gradient from 0% acetonitrile over 3 minutes, 0% to 15% over 7 minutes, 15% to 65% over 42 minutes, 65% to 90% over 5 minutes and, lastly, 6 minutes in 90% of acetonitrile. The flow rate was set to 300 nL/min and 110 fractions were automatically collected every 30 seconds on an AnchorChip™ MALDI target using a Proteineer™ FC fraction collector (Bruker Daltonics, Germany). Two µl of α-cyano-4-hydroxycinnamic acid matrix (0.3 mg/mL in acetone:ethanol:0.1% TFA-acidified water, 3:6:1 v/v/v) were added during the collection process. The MS and MS/MS mass measurements were performed off-line using the Ultraflex™ II TOF/TOF mass spectrometer (Brucker Daltonics). The apparatus parameters were set to values given below. Peptide fragmentation was driven by Warp LC™ software (Bruker Daltonics) according to the following parameters: signal-to-noise ratio>15, more than 3 MS/MS by fraction if the MS signal was available, 0.15 Da of MS tolerance for peak merge and elimination of peaks which appears in more than 35% of the fractions. The protein identification was performed as described below.

Mass Spectrometry

The molecular mass measurements were performed in automatic mode using the FlexControl™ 3.0 software on an Ultraflex™ II TOF/TOF instrument and in reflectron mode for MALDI-TOF peptide mass fingerprinting (PMF) or "LIFT" mode for MALDI-TOF/TOF peptide fragmentation fingerprinting (PFF). External calibration over a 1000-3200 mass range was performed using the [M+H]+ monoisotopic ions of bradykinin 1-7, angiotensin I, angiotensin II, substance P, bombesin and adrenocorticotropic hormone (clip 1-17 and clip 18-39) using a peptide calibration standard kit (Bruker Daltonics). Briefly, an accelerating voltage of 25 kV, a reflector voltage of 26.3 kV and a pulsed ion extraction of 160 ns were used to obtain the MS spectrum. Each spectrum was produced by accumulating data from 800 laser shots. A maximum of five precursor ions per sample were chosen for LIFT-TOF/TOF MS/MS analysis. Precursor ions were accelerated to 8 kV and selected in a timed ion gate. Metastable ions generated by laser-induced decomposition were further accelerated by applying 19 kV in the LIFT cell and their masses were measured in reflectron mode. Peak lists were generated from MS and MS/MS spectra using Flexanalysis™ 3.3 software (Bruker Daltonics). Database searches with Mascot 2.3.02 (Matrix Science Ltd, London, UK) using combined PMF and PFF datasets were performed in the UnitProt 2012_06_database via ProteinScape™ 2.1 (Bruker Daltonics). Taxonomy was restricted to Human in raison of the protein source nature. A mass tolerance of 75 ppm and 1 missing cleavage site for PMF and an MS/MS tolerance of 0.5 Da and 1 missing cleavage site for MS/MS searching were allowed. Carbamidomethylation of cysteine and oxidation of methionine residues were considered as fixed and variable modifications, respectively. The relevance of protein identities was judged according to the probability-based MOlecular Weight SEarch (MOWSE) score calculated with a p value equal or lower than 0.05 ($p<0.05$).

Western Blotting

After electrophoresis, proteins were transferred to 0.45 µm nitrocellulose membrane (Amersham, Life Science GE Healthcare, Piscataway N.J. USA) using the NuPage Liquid Transfer System (Life Technologies) and according to the manufacturer's instructions. Membranes were blocked with a solution containing 5% skimmed milk-TNT (Tris-HCl15 mM pH 8.0-NaCl 140 mM, 0.05% (w/v) Tween-20). Membranes were incubated with the primary antibodies overnight at 4° C. (complete antibody references and dilutions are listed in Table 1). Immuno-complexes were revealed after incubation with secondary antibodies coupled to horseradish peroxidase (horse anti-mouse: 1/50000 in TNT or goat anti-rabbit: 1/5000 in TNT, Vector Laboratories, Burlingham USA) and detected using the ECL™ luminescence kit (Amersham, Life Science GE Healthcare, Piscataway N.J. USA). The luminescence of immune-complexes was acquired with a LAS3000 imaging system (Fujifilm).

TABLE 1

Proteins, manufacturers, species and dilutions of the primary antibodies used in western-blotting and immunocytochemistry.

| Antibody | Manufacturer | Epitope | Species | Dilution Immunoblotting | Dilution Immunocyto-chemistry |
|---|---|---|---|---|---|
| Proacrosin | mAb 4D4 (Gallo et al., 1991) | C-ter | Mouse | 1/1000 - TNT | — |
| Histone H3 | 05 - 928 (Millipore, Bellerica, USA) | C-ter of total H3 independant of post-translational modifications | Rabbit | 1/2000 - TNT | — |
| HSP 90 | Sc 13119 - A1510 (Santa Cruz, California, USA) | Amino acids 610-723 | Mouse | 1/500 - TNT | — |
| Cytochrome C | 89515 (BD Pharmingen, San José, USA) | — | Mouse | 1/500 - TNT | — |
| GAPDH | Sc25778 FL335 (Santa Cruz, California, USA) | Amino acids 1-335 | Rabbit | 1/10000 - TNT | — |
| Tubulin β | MAb 3408 - LV 1475931 (Millipore, Bellerica, USA) | — | Mouse | 1/10000 - TNT | — |
| AKAP4 N-ter | Ab 56551 (Abcam, UK) | Amino acids 1-101 | Mouse | 1/10000 - TNT | 1/500 - TBS 1X |
| AKAP4 C-ter | Sc-66308 (Santa Cruz, California, USA) | C-ter | Goat | 1/5000 - TNT | 1/400 - TBS 1X |
| Hexokinase 1 N-ter | Ab 55144 (Abcam, UK) | Amino acids 101-201 | Mouse | 1/5000 - TNT | 1/200 - TBS 1X |
| Hexokinase 1 C-ter | Sc-6518 (Santa Cruz, California, USA) | C-ter | Goat | 1/1000 - TNT | 1/100 - TBS 1X |

TNT = Tris-NaCl-Tween.
TBS = Tris Buffer Saline

Immunochemistry

After sperm isolation, 100 µL of homogenate were fixed with 2% paraformaldehyde and incubated 15 min at room temperature. Spermatozoa were isolated by centrifugation (10 min, 350×g) and supernatant was removed. Sperm pellet was suspended in TBS 1× and washed by centrifugation two times (10 min, 350×g). Sperm pellet was suspended in 100 µL of TBS 1×. Thick drop was dropped-off on Superfrost slide (Menzel-Glazer, Germany) and conserved at 4° C.

Slides were placed in acetone bath during 5 min at ambient temperature and washed twice in TBS 1× (5 min). 100 µL of TBS 1×-BSA 0.2% were deposed on thick drop and slides were incubated 1 h at room temperature. 100 µL of primary antibody diluted in TBS 1× (Table 1) covered thick drop and slides were incubated at 4° C. overnight. Slides were washed two times 5 min in TBS 1× at room temperature. Secondary antibodies (Vector Laboratories, Cliniscences, SAS France) were diluted in TBS 1× and slides were incubated during 1 h at room temperature. Slides were washed twice 5 min in TBS 1×. ABC mixture (Vectastain ABC Kit, Vector Laboratories) covered slides according to manufacturer's instructions. Immunolocalization was revealed by DAB (Vectastain ABC Kit) and reaction was stopped with water. Sperm head was stained with hematoxylin Mayer's solution (SIGMA-Aldrich, France) during 1 min. Slides were placed in successive bath of ethanol 70/95/100% during 1 min/bath and toluene bath (10 min). Slides were mounted with the VectaMount™ AQ Mounting Medium (Vector Laboratories). Images from slides were obtained with a Leica DM 2000 LED microscope (Leica, France).

AKAP4 Sandwich ELISA

Nunc F8 Maxisorp 96-well plates (Ref. 469949) are coated overnight at 4° C. with a 1/500 (volume/volume) dilution of AKAP4 C-terminus antibody (Santa Cruz Calif., Sc-66308 Goat polyclonal antibody). Wells are rinsed twice with PBS (Phosphate Buffer Saline pH 7.4, P3813 Sigma-Aldrich) Tween-20 (0.05%) and saturated with 200 µl of PBS added with 0.1% casein (weight/volume) during 1 hour at 37° C. Before incubation with the sperm sample, the plate is rinsed twice with PBS Tween-20 (0.05%). Sperm sample is diluted at 1/2000 in PBS and 100 µl is incubated in the plate overnight at 4° C. The plate is rinsed twice in PBS and incubated 2 hours at room temperature with the AKAP4 monoclonal antibody (Abcam, UK, Ab 55144, mouse monoclonal antibody) diluted at 1/500 in PBS added with 0.2% BSA (weight/volume). The plate is rinsed twice with PBS Tween-20 (0.05%) and incubated with horseradish peroxidase coupled anti-mouse IgG gamma-chain (Sigma-Aldrich, Ref A3673) at 1/4000 in PBS BSA (0.2% weight/volume) during one hour at 37° C. The immune-complexes are rinsed twice with PBS Tween-20 (0.05%) and the reaction is revealed with TMB (Sigma-Aldrich ref. T3405) in citrate/phosphate buffer pH 5 added 2 µl of $H_2O_2$ at 30%. After 30 minutes at room temperature, the reaction is stop with 50 µl of $H_2SO_4$ solution (10.32 mL, of $H_2SO_4$ in 89.78 mL of $H_2O$). The optical density is measured at 450 nm. A standard curve of recombinant AKAP4 is performed with a serial dilution from 1.2 ng to 0.36 ng in PBS.

Biostatistics Analysis

Quantitative data are presented as mean with standard deviation. Quantitative data were analyzed and compared using the SAS software release 9.01 (SAS Institute INC, Cary, N.C.). SPQI Group A and B were compared in terms of age, sperm volume, cell count and motility. Pearson correlation coefficient was calculated to evaluate relationship between sperm parameters and age of men. Anova (variance analysis) and Student t-test (average analysis) were used to analyze the relationship between SPQI and semen parameters. Statistical significance was set at $p<0.05$ for all tests.

Results

Sperm Isolation and Analysis of Sub-Cellular Markers

For the present study, 161 human semen samples were freshly collected. Men were aged of 34.7±5.8 years old (22-56) on average. Individuals had no infectious disease or treatment that could interfere with semen parameters. For all samples, the semen volume was over the lower limits of 1.5 mL (WHO 2010). The initial number of spermatozoa counted was of 101 $10^6$±65.5 $10^6$ spermatozoa/mL on average (385 $10^6$±295 $10^6$ spermatozoa/ejaculate) and therefore above the lower reference average limit of 15 $10^6$ spermatozoa/mL. The PR motility was of 51.27%±12.27% over the lower reference limit of 32%. Normal spermatozoa morphology was of 33.8%±12.5% above lower reference limit of 4%. After selection, no epithelial or round cells were detected as established by light microscopy assessment of spermatozoa from crude and gradient isolation.

Although the protocol for the isolation of spermatozoa was routinely used in clinic, molecular markers of the sperm compartments were evaluated. Thus, the microscopic observation of spermatozoa was associated to the analysis of protein markers of spermatozoa sub-compartments: proacrosin for the acrosome, histone H3 for the nucleus, HSP90 for the cytoplasm, cytochrome C for mitochondria and tubulin-β for the flagellum. This analysis was performed in five individual sperm protein samples. Proacrosin was resolved as a single band at 50 kDa. Proacrosin was not detected in T98 protein lysate. Histone H3 (17 kDa), HSP90 (90 kDa), Cytochrome C (15 kDa) and Tubulin-β (50 kDa) were detected both in protein lysate from sperm and T98 cells. Histone H3 and Tubulin-β were proportionally more abundant in spermatozoa than in T98 glioblastoma-derived cells. Together, the microscopic and molecular markers analyses did not show obvious alteration of spermatozoa following our isolation protocol.

Spermatozoa 1D Proteome Pattern

Whereas equal amounts of proteins were loaded, two major protein profiles were observed in Coomassie blue stained of 1D SDS-PAGE gels. The inventors observed that 49.6% of sperm samples (80/161) presented many and several well-individualized intense bands comprised between 15 to 160 kDa and this group of electrophoretic protein pattern was defined as group A. In contrast, 50.4% of sperm samples (81/161) were included in the group B characterized principally by the lower level or absence of the strong band at 110 kDa apparent molecular weight. Higher molecular weights polypeptides were also less intensively stained in this group B 1D protein pattern. To further analyze the profiles of human sperm protein expression, proteins with apparent molecular weights were selected such as histone H3 (17 kDa), GAPDH (37 kDa), tubulin-β (50 kDa) and HSP90 (90 kDa). Strong signals were detected for these proteins in sperm protein lysate from group A as well as in T98 glioblastoma cells. Histone H3 staining was comparable in both group A and group B. A decreased signal of GAPDH, tubulin-β and HSP90 were observed in sperm protein lysates from group B.

Mass Spectrometry Identification of Proteins Contained in 110 kDa Bands in Coomassie Blue Strained 1D SDS-PAGE Gel The protein electrophoretic pattern of group B was suggestive of a proteolysis of polypeptides during spermatozoa isolation. Proteolysis of sperm proteins during protein extraction or due to a defective quantification was ruled out. Thus addition or protease inhibitors following sperm liquefaction or the loading of increasing volumes of protein samples did not modified the electrophoretic protein pattern. High molecular weights polypeptides and especially the intensively Coomassie blue stained band at 110 kDa was poorly stained and therefore, the Coomassie Blue-stained band was isolated and polypeptides present in this band were analysed by mass spectrometry. Two proteins were identified by Nano-LC MS/MS in the 110 kDa Coomassie-stained band of group A sample. These proteins corresponded to the A-kinase anchor protein 4 (AKAP4) and hexokinase-1 (HK1) (Table 2).

TABLE 2

Identification of proteins contained in 110 kDa bands following in gel trypsic digestion of the polypeptides and mass spectrometry identification.

| Accession | MW [kDa] | pI | Score | #Pept. | SC [%] | Protein |
|---|---|---|---|---|---|---|
| AKAP4_HUMAN | 94.4 | 6.6 | 377.5 | 5 | 8.7 | A-kinase anchor protein 4 OS = *Homo sapiens* GN = AKAP4 |
| HXK1_HUMAN | 102.4 | 6.4 | 118.6 | 2 | 3.2 | Hexokinase-1 OS = *Homo sapiens* GN = HK1 |

MW = Theoretical molecular weight;
pI = isoelectric point;
Score = identification score:
Pept. = number of peptide sequenced;
SC = overlap with the protein sequence (%).

AKAP4 and HK1 Profile Explored by Immunoblotting

AKAP4 and HK1 expression was analyzed by immunoblotting in more than 30 samples from group A and from group B (FIG. 1) with antibodies directing against N-ter and C-ter parts of both proteins. A single band at 85 kDa and 110 kDa corresponding to AKAP4 and HK1 respectively was detected in all human sperm samples from group A with antibody directing against N-ter part of both proteins. Two bands at 85 and 95 kDa corresponding to pro-AKAP4 and AKAP4 were observed in sperm samples from group A with a C-ter antibody. In sharp contrast, AKAP4 and HK1 were not or poorly detected in samples from group B. Instead of the 110 kDa band, several bands with molecular weights lower than 110 kDa were visualized for both proteins in group B samples whatever antibodies used but were different (FIG. 1). No signal corresponding to AKAP4 was detected in T98 cells lysate suggesting that the band detected in sperm protein is not artefactual. Our results strongly suggest that the 110 kDa bands observed by Coomassie Blue staining contain the AKAP4 and HK1 proteins and the disappearance of staining is likely related to change in AKAP4 and HK1 expression in group B samples when compared to group A.

Sub-Cellular Localization of AKAP4 and HK1 by Immunochemistry

AKAP4 and HK1 sub-cellular localization were analyzed by immunochemistry. As ever described in literature (Eddy, Toshimori, and O'Brien 2003), both proteins were located in fibrous sheath of sperm sperm flagellum. Any differences were observed between group A and B.

Sperm Protein Quality Index (SPQI)

After numerical analyses of Coomassie blue stained gels with Image J (FIG. 2A), bands with the strongest intensities were used to compare the 161 human sperm protein samples. Two windows of molecular weight were defined. Thus, protein bands between 15 to 30 kDa (Low molecular weights LMW) and secondly bands between 80 to 110 kDa (high molecular weights HMW) were selected. These two windows were reproducibly defined using molecular weight markers to calibrate the gels. Each band visualized on gel was defined as a pic by the software (FIG. 2B). For each window, area under curve was calculated (FIG. 2C). To establish a sperm proteome quality index (SPQI), the ratio between the area under curve from HMW and LMW band intensities (FIG. 2D) was calculated. When the 1D proteome was resolved as numerous intense protein bands over the whole 1D SDS-PAGE lane, the ratio was comprised between 1 and 2, named SPQI A and represented 80/161 samples. A second category of proteome profiles with a SPQI B below 1 or above 2 included 81/161 samples was defined.

SPQI and Sperm Parameters

Any correlation between sperm parameters and the age of men was revealed in whole population. With regards to the SPQI, the sperm parameters were reported. Group A were classified with a SPQI A (Table 3) whereas group B had an SPQI B (Table 3). SPQI B group (n=80, 35.6 years old) was 1.9 years older on average than SPQI A group (n=81, 33.7 years old). The number of spermatozoa per mL of semen (SPQI A=111.8 $10^6$±72 spz/mL vs SPQI B 90.5 $10^6$±56 spz/mL, p=0.041) as well as the PR motility (SPQI A=53.9±9% vs SPQI B 48.6±14%, p=0.006) were significantly higher for SPQI A than for SPQI B (Table 3). The PR motility showed the strongest statistical difference between SPQI A and B. Sperm morphology was not different between the two groups.

TABLE 3

Sperm parameters related to the 1-D sperm proteome index.

| Sperm parameters | SPQI A (n = 80) Mean ± SD (min-max) | SPQI B (n = 81) Mean ± SD (min-max) | P (t-test) |
|---|---|---|---|
| Age (years) | 33.7 ± 5.1 (22-46) | 35.6 ± 6.3 (23-56) | 0.043 |
| Volume (mL) | 3.7 ± 2.2 (1.5-5.9) | 4.2 ± 1.1 (1.9-5.7) | NS |
| Sperm count ($10^6$/mL) | 111.8 ± 72.4 (23.9-380) | 90.5 ± 56.3 (15.5-300) | 0.041 |

TABLE 3-continued

Sperm parameters related to the 1-D sperm proteome index.

| Sperm parameters | SPQI A (n = 80) Mean ± SD (min-max) | SPQI B (n = 81) Mean ± SD (min-max) | P (t-test) |
|---|---|---|---|
| Progressive motility (%) | 53.9 ± 9.4 (40-70) | 48.6 ± 14.1 (35-70) | 0.006 |
| Normal sperm morphology (%) | 33.6 ± 11.8 (17-65) | 33.9 ± 13.1 (16-58) | NS |

SPQI = Sperm Protein Quality Index;
SD = Standard Deviation;
NS = No Significant.

Full-Length AKAP4 Sandwich ELISA

In order to discriminate between group A and group B, the inventors have developed an ELISA with a C-terminus goat anti-AKAP4 antibody and a N-terminus mouse monoclonal anti-AKAP4 to reveal. Accordingly to our observations, AKAP4 proteolysis occur at the C-terminus of the protein. The ELISA would therefore enable to quantify the amount of full-length AKAP4 whereas, the proteolysis of AKAP4 would lead to a reduce amount of the full-length and therefore a lower level of detection. Thus, the inventors expected to detect subject from the group A and a reduced amount of AKAP4 should be detect in group B. The inventors first determined the functionality of the assay using incremental quantity of the human recombinant AKAP4 protein. The sandwich ELISA enables the detection of 10 ng of recombinant protein and reach a plateau over 100 of ng (FIG. 3A). Using the assay, the quantity of AKAP4 was measured in serial dilution of sperm sample from a subject of the group A and one subject of the group B. In the sperm sample of the group A, the DO was increasing from dilution of 1/10000 to 1/1000. In sharp contrast, the DO only slightly increases in sperm sample from the subject of group B. Noticeably, at a dilution of 1/2000 the DO was of 0.7 for the sample of group A whereas the DO was of 0.47 for the sample of the group B subject, knowing that the basal background signal is of 0.35. This results therefore shows that a sandwich ELISA using a C-terminus anti-AKAP4 antibody to capture the protein enable to discriminate between the two groups.

Distribution of SPQI Group A and B in ART and Success of Birth

To date, among the 161 couples that were followed at the Lille Hospital Fertility department, ART has been offered to 150 (93.1%) of them. Intrauterine insemination (IUI) has been performed in 76 couples, current in vitro fecondation (IVFc) was performed in 60 couples and 14 of them were proposed intracytoplasmic sperm injection (ICSI). Independently of the ART proposed to patients, frequency of birth success between group A (34%) and group B (22%) was slightly higher for group A. However, differences were more pronounced depending of the ART performed. Thus, among couples with IUI 19 birth were observed. The frequency of success was not significantly differently between categorized in group A (8/35; 23%) or group B (11/41; 27%). Among couples with IVFc, 42.8% (15/35) of success was observed with men belonging to group A whereas a lower frequency of success (28%, 7/25) for men of the group B. Interestingly, among couples with ICSI, 6 births were obtained 2/3 (66.6%) for men included in the group A and 4/11 (36.3%) for men in the group B.

Discussion

In order to further investigate the potential modification of the sperm proteome that could be associated to the sperm quality index, a simple biochemical method enabling to define a sperm proteome quality index, herein named SPQI, based on analysis of the whole 1D sperm proteome profile and/or proteolysis of two major sperm proteins AKAP4 and Hexokinase 1 have been designed. Over the analysis of sperm proteomes from 161 ejaculates with normal sperm parameters widely above lower references limits given by WHO (World Health Organization 2010), two categories of proteome profiles were established and a modification of this proteome was identified. SPQI is significantly correlated with lower progressive motility of spermatozoa. To the best our knowledge, it is the first study to report a modified 1D proteome profile in normozoospermic samples significantly associated with a change in the progressive motility of spermatozoa in men with normozoospermia.

A method was set up to select most sperm cells and extract sperm protein. Currently, they are two methods to isolate spermatozoa, the swim-up method and the density gradient. The swim-up method selects the most motile spermatozoa. However, to study the whole sperm proteome from ejaculate the lower selection of spermatozoa was necessary. A single-step density gradient centrifugation method was used to isolate spermatozoa from seminal plasma and round cells. Moreover, culture medium for spermatozoa used for sperm washing contains protein such as albumin and was replaced by a Tris buffer. In sperm pellet, round cells were rarely or often not observed and the morphology of spermatozoa was preserved. To evaluate protein extraction and protein integrity, markers from every sperm cell compartment were explored. For example, proacrosin belongs to acrosome and is cleaved in active form as β-acrosin during acrosomal reaction or consequently to sperm manipulation (Gallo et al. 1991; Zahn et al. 2002). After sperm selection proacrosin was visualized as well by immunoflurorescence (not shown) and detected by immunoblotting in sperm lysates. Together, these proteins were detected in sperm protein lysates, these data suggest that method is not selective from one cell-compartment and molecular integrity was preserved.

After lysis and protein extraction, the protein quantity loaded for 1D SDS-PAGE was equal for all samples. However, the 1D SDS-PAGE profile is different. To exclude the possibility that the differences between 1D protein profiles could not result from an artifact from the method used to determine the protein concentration, BCA or the Bradford methods for protein quantification were compared. Both were giving similar sperm proteome profile. However, protein concentration determined with a kit does not indicate on the integrity of the polypeptide. Moreover, some sperm protein profile were characterized by the loss of Coomassie blue stained polypeptides of molecular weights over 50 kDa, an explanation could be that sperm proteins might be degraded during liquefaction or sperm selection. Therefore, all samples were freshly prepared after recovering ejaculates and the liquefaction time was systematically of 30 minutes. Protease inhibitors were added or not after semen liquefaction but addition or these protease inhibitors did neither improve the protein profile nor increase the number of polypeptides bands. Taken together, these observations suggest that is the protein profile observed in group B is resulting from the partial proteolysis of sperm proteome, it may possibly occur during liquefaction.

Despite having normal sperm parameters, sperm is a heterogeneous complex fluid with a variable number of abnormal spermatozoa. Without having an experimental explanation to explain the difference between 1D SDS-PAGE profile, two groups were defined according to the 1D proteome quality. The group A included samples with many intense and homogeneous bands visualized between 15 to 110 kDa. Group B represented samples that showed a decrease or a disappearance of high molecular weight proteins, with regards to the sensitivity of Coomassie blue staining Bands from 110 kDa of 1D-SDS PAGE coomassie blue staining gel was analyzed and characterized by mass spectrometry. AKAP4 and Hexokinase 1 were significantly identified and there expressions were explored by western blotting. Group A presented a single band for both proteins at about 100 kDa corresponding to protein expression. Group B showed many bands from 20 to 50 kDa and 25 to 50 kDa for AKAP4 and Hexokinase 1 respectively suggesting a modification of these protein expressions. Histone H3 expression was not disturbed regardless of profile. This can be explained by biochemical proprieties of this basic protein (pI>11). Indeed, proteases implied in this elimination are probably different from the other proteins of spermatozoa, that is why we could observe no differences in its expression in our samples. Hexokinase 1 is a predominant glycolytic enzyme presents in spermatozoa (Eddy, Toshimori, and O'Brien 2003; Nakamura et al. 2008). It is mainly localized in fibrous sheath of spermatozoa and uses ATP to phosphorylate glucose to glucose-6-phosphate necessary for sperm motility. AKAP4 is a structural protein identified in fibrous sheath and that binds cAMP-dependant-kinase (PKA) to initiate and mediate sperm motility (Brown 2002; Moretti et al. 2007). Its protein is encoded by a X-linked genes into a precursor: pro-AKAP4 (97 kDa) that cleaves in AKAP4 (82 kDa) (Turner et al. 1998; Eddy, Toshimori, and O'Brien 2003). Men with dysplasia of fibrous sheath presents a gene sperm defect resulting in short or irregular flagella with disorganized axonemes (Baccetti 2005a; Baccetti 2005b; Baccetti et al. 2005). Immunostaining of sperm samples with AKAP4 antibody showed an incomplete assembled fibrous sheath scaffold (Baccetti et al. 2005). Molecular analysis demonstrated a mutation in gene that encoded AKAP4 (Turner et al. 2001; Baccetti 2005b). Recently, Xu et al. showed an down-regulation of AKAP4 in infertile normozoospermic men (Xu et al. 2012). According to literature, bands observed in our immunoblotting in Group B did not result from maturation of pro-AKAP4 to AKAP4. Netherthless, immunochemistry did not revealed differences in localization for both proteins between Groups A and B. Moreover, sperm morphology was not modified. Our results suggest a proteolysis of AKAP4 and hexokinase 1 in group B independently of sperm morphology. Proteolysis is a known to be as physiological phenomenon in spermatozoa. Ubiquitin dependent proteolysis is one of most important pathways implied in spermatogenesis, sperm quality control and fertilization (Sutovsky 2003; Sutovsky 2011). Moreover, proteasome mediated proteolysis implied in acrosomal reaction and digestion of vitelline membrane (Zimmerman and Sutovsky 2009; Rawe et al. 2008; Kong, Diaz, and Morales 2009). After fertilization, some proteins get an ubiquitin-tag as prohibitin, to be eliminated by oocyte (Thompson 2003). Proteasome pathways could be implied in proteolysis of AKAP4 and hexokinase 1.

After analysis with ImageJ software, a quality index was determined and its relationship with sperm parameters was evaluated by biostatistical analysis. Two homogenous groups were constituted. Group A presents a quality index comprised between 1 to 2 corresponding to an homogeneous sperm protein profile in every molecular weight. Group B contained samples characterized by sperm proteome with a disappearance of bands from high molecular weight translated by a quality index lower/over than 1 or 2. Average from each sperm parameters considered as fertility markers (count of cells, motility and morphology of spermatozoa) were compared in both groups. Progressive motility appears to be strongly significantly different in group A compared with group B. Together, these results suggest that SPQI are a marker of progressive motility of spermatozoa and in relationship with a modification of AKAP4 and Hexokinase 1 expression.

In conclusion, in the present invention, the inventors suggest that the sperm proteome quality index may represent a good in vitro assay to evaluate sperm quality. This SPQI relies on the integrity of two major sperm proteins AKAP4 and Hexokinase 1. Their proteolysis may serve as an important indicator of lower progressive motility and more widely of sperm quality and used to understand mechanism of unknown sperm dysfunction. Actually, WHO criteria 2010 recommend a decrease of normal value for sperm parameters particularly for motility and morphology. Our results suggest that better sperm parameters are correlated with our biochemical quality index. Moreover, our preliminary data with regards to the success at birth in between group A and group B using ART suggest a general higher success rate for men of group A and even more obviously for IVFc and IUI technics while may recommend IUI for group B men since the rate of success is very similar to that observed in group A. Altogether, our data suggest that the sperm quality index could really useful to associated with current laboratory sperm analysis in order to further predict the chance of conceive success in ART.

Example 2

Comparison of IIU Outcome Variables According to the Groups A and B

The proteolyzed profile (group B) is indicative of a bad prognosis and bad sperm quality. The group B is associated with bad indicators such as higher number of biochemical pregnancy, abortion (miscarriage) than group A (Table 5).

TABLE 4

Sperm parameters of semen samples according to the groups A (1D-SDS PAGE, non-proteolyzed proteome) and B (proteolyzed proteome)

|  | Group A (mean ± SD) n = 37 | Group B (mean ± SD) n = 38 | p | WHO 2010 recommandations |
|---|---|---|---|---|
| Volume (ml) | 3.5 ± 1.1 | 3.6 ± 1 | NS | >1.5 |
| Sperm count ($\times 10^6$/mL) | 110 ± 60.2 | 108.1 ± 74.6 | NS | >15 |
| Sperm count ($\times 10^6$/ejac) | 369.8 | 399.4 | NS | >39 |
| Ratio sperm count (mL/ejac) | 0.3 | 0.3 | NS | / |
| Progressive motility (a + b)(%) | 54.2 ± 9.7 | 49.1 ± 11.3 | 0.03 | >32 |

TABLE 4-continued

Sperm parameters of semen samples according to the groups A (1D-SDS PAGE, non-proteolyzed proteome) and B (proteolyzed proteome)

| | Group A (mean ± SD) n = 37 | Group B (mean ± SD) n = 38 | p | WHO 2010 recommandations |
|---|---|---|---|---|
| Normal morphology (%) | 36.9 ± 14 | 34.4 ± 12.2 | NS | 15 |
| MAI | 1.6 ± 0.1 | 1.6 ± 0.2 | NS | <1.6 | mL, millilitter;
ejac, ejaculation;
MAI, multiple abnormalities index;
NS, non significant;
WHO, world health organization

TABLE 5

Comparison of IIU outcome variables according to the groups A and B

| | Group A (mean ± SD) n = 37 | Group B (mean ± SD) n = 38 | p |
|---|---|---|---|
| Patient age (yrs) | 33.8 ± 4.5 | 35.6 ± 5.6 | NS |
| BMI patient | 27.1 ± 3 | 25.2 ± 3.3 | NS |
| BMI partner | 23.6 ± 3.9 | 24.9 ± 5.3 | NS |
| Tobacco patient (cig/d) | 4.6 | 5.4 | NS |
| Tobacco partner (cig/d) | 1.1 | 0.8 | NS |
| Duration of infertility (yrs) | 3.5 ± 2.1 | 5.1 ± 3.2 | NS |
| Total cycles (n) | n = 116 | n = 106 | |
| Cycles | 3.1 ± 1.8 | 2.8 ± 1.5 | NS |
| Biochemical pregnancy (%) | 9.5 | 20.7 | 0.02 |
| Clinical pregnancy (%) | 6.9 | 10.4 | NS |
| Delivery (%) | 6 | 10.4 | NS |
| Abortion (%) | 3.5 | 10.3 | 0.04 |

SD, standard deviation;
yrs, years;
BMI, Body mass index;
cig/d, cigarettes/day;
n, number;
NS, non significant Example 3

Comparison of IVF/ICSI Outcome Variables According to the Groups A and B

The group A is significantly associated with a higher embryo quality, embryo implantation, pregnancy and delivery than the group B (Table 7).

TABLE 6

Sperm parameters of semen samples according to the groups A and B

| | Group A (mean ± SD) n = 38 | Group B (mean ± SD) n = 35 | p | WHO 2010 recommandations |
|---|---|---|---|---|
| Volume (mL) | 4 ± 1.8 | 3.7 ± 1 | NS | >1.5 |
| Sperm count (×10⁶/mL) | 105.4 ± 75.5 | 92.8 ± 67.2 | NS | >15 |
| Sperm count (×10⁶/ejac) | 404 ± 352.4 | 335 ± 258.3 | NS | >39 |
| Ratio sperm count (mL/ejac) | 0.3 ± 0.1 | 0.3 ± 0.1 | NS | / |
| Progressive motility (a + b) (%) | 52.5 ± 10 | 47.7 ± 15.6 | NS | >32 |
| Normal morphology (%) | 35.2 ± 11.3 | 32.4 ± 15.4 | NS | 15 |
| MAI | 1.6 ± 0.1 | 1.6 ± 0.2 | NS | <1.6 | mL, millilitter;
ejac, ejaculation;
MAI, multiple abnormalities index;
NS, non significant;
WHO, world health organization

TABLE 7

Comparison of IVF/ICSI outcome variables according to the groups A and B

| | Group A (mean ± SD) n = 38 | Group B (mean ± SD) n = 35 | p |
|---|---|---|---|
| Patient age (yrs) | 34.1 ± 4.8 | 36.2 ± 6 | NS |
| Partner age (yrs) | 30.3 ± 3.8 | 33.1 ± 4.4 | NS |
| BMI patient | 27.4 ± 1.5 | 23.8 ± 1.7 | NS |
| BMI partner | 22.8 ± 3 | 23 ± 4.5 | NS |
| Tobacco patient (cig/d) | 6 | 8 | NS |
| Tobacco partner (cig/d) | 4 | 3 | NS |
| Duration of infertility (yrs) | 4.2 ± 1.4 | 4.6 ± 2 | NS |
| Total cycles (n) | n = 63 | n = 64 | |
| Cycles | 1.7 ± 0.8 | 1.8 ± 1 | NS |
| Total oocytes retrieved | 9.2 ± 5.5 | 7.5 ± 3.6 | NS |
| Atretic oocytes | 1 ± 1.6 | 0.6 ± 1.1 | NS |
| Immature oocytes | 1 ± 1.9 | 1.1 ± 1.3 | NS |
| Injected oocytes | 7 ± 4.4 | 5.8 ± 3.2 | NS |
| Pronuclear assessment | | | |
| 1PN | 0.2 ± 0.5 | 0.2 ± 0.6 | NS |
| 2PN | 5.4 ± 3.6 | 4.4 ± 2.8 | NS |
| Polyploid | 0.3 ± 0.6 | 0.3 ± 0.6 | NS |
| Fertilization rate (%) | 79 ± 20 | 77 ± 22 | NS |
| Early clivage (%) | 48 ± 39 | 52 ± 0.4 | NS |
| Total embryos produced (n) | n = 321 | n = 269 | |
| Embryos | 5.1 ± 3.3 | 4.2 ± 2.7 | NS |
| Embryo quality | | | |
| A | 1.6 ± 1.8 | 0.9 ± 1.1 | 0.017 |
| B | 0.2 ± 0.5 | 0.2 ± 0.5 | NS |
| C | 3.2 ± 2.7 | 3.1 ± 2.3 | NS |
| Freezed embryos | 1.8 ± 2 | 1 ± 1.7 | 0.01 |
| Total embryos tranfered | 1.2 ± 1.9 | 1.1 ± 1.9 | NS |
| Clinical pregnancy (%) | 44 ± 50 | 19 ± 39 | 0.002 |
| Delivery (%) | 39 ± 49 | 19 ± 39 | 0.01 |
| Implantation (%) | 27 ± 42 | 12 ± 32 | 0.006 |
| Abortion (%) | 10 ± 30 | 6 ± 24 | NS |

SD, standard deviation;
yrs, years;
BMI, body mass index;
cig/d, cigarettes/day;
n, number;
NS, non significant;
PN, pronucleus

REFERENCES

Throughout this application, various references describe the state of the art to which this invention pertains. The disclosures of these references are hereby incorporated by reference into the present disclosure.

Aitken, R J. 2006. "Sperm Function Tests and Fertility." International Journal of Andrology 29 (1) (February): 69-75. doi:10.1111/j.1365-2605.2005.00630.x.

Aitken, R J. 2011. "The Capacitation-Apoptosis Highway: Oxysterols and Mammalian Sperm Function." Biology of Reproduction 85 (1) (June 24): 9-12. doi:10.1095/biolreprod.111.092528.

Aoki, Vincent W, Lihua Liu, Kirtly P Jones, Harry H Hatasaka, Mark Gibson, C Matthew Peterson, and Douglas T Carrell. 2006. "Sperm Protamine 1/Protamine 2 Ratios Are Related to in Vitro Fertilization Pregnancy Rates and Predictive of Fertilization Ability." Fertility and Sterility 86 (5) (November): 1408-1415. doi:10.1016/j.fertnstert.2006.04.024.

Baccetti, B. 2005a. "Gene Deletions in an Infertile Man with Sperm Fibrous Sheath Dysplasia." Human Reproduction (Oxford, England) 20 (10) (June 24): 2790-2794. doi:10.1093/humrep/dei126.

Baccetti, B. 2005b. "Gene Deletions in an Infertile Man with Sperm Fibrous Sheath Dysplasia." Human Reproduction (Oxford, England) 20 (10) (June 24): 2790-2794. doi:10.1093/humrep/dei126.

Baccetti, Baccio, Giulia Collodel, Laura Gambera, Elena Moretti, Francesca Serafini, and Paola Piomboni. 2005. "Fluorescence in Situ Hybridization and Molecular Studies in Infertile Men with Dysplasia of the Fibrous Sheath." Fertility and Sterility 84 (1) (July): 123-129. doi:10.1016/j.fertnstert.2005.01.128.

Blomberg Jensen, M, A Jørgensen, J E Nielsen, P J Bjerrum, M Skalkam, J H Petersen, D L Egeberg, et al. 2012. "Expression of the Vitamin D Metabolizing Enzyme CYP24A1 at the Annulus of Human Spermatozoa May Serve as a Novel Marker of Semen Quality." International Journal of Andrology (March 9): no-no. doi:10.1111/j.1365-2605.2012.01256.x.

Bresler, Kristin, Susanne Pyttel, Uwe Paasch, and Jürgen Schiller. 2011. "Parameters Affecting the Accuracy of the MALDI-TOF MS Determination of the Phosphatidylcholine/Lysophosphatidylcholine (PC/LPC) Ratio as Potential Marker of Spermatozoa Quality." Chemistry and Physics of Lipids 164 (7) (October 1): 696-702. doi:10.1016/j.chemphyslip.2011.07.006.

Brown, P R. 2002. "A-Kinase Anchoring Protein 4 Binding Proteins in the Fibrous Sheath of the Sperm Flagellum." Biology of Reproduction 68 (6) (December 27): 2241-2248. doi:10.1095/biolreprod.102.013466.

Chaudhury, Koel, Tuhin Das, Baidyanath Chakravarty, and Asok K Bhattacharyya. 2005. "Acrosin Activity as a Potential Marker for Sperm Membrane Characteristics in Unexplained Male Infertility." Fertility and Sterility 83 (1) (January): 104-109. doi: 10.1016/j.fertnstert.2004.06.063.

Cocuzza, Marcello, Suresh C Sikka, Kelly S Athayde, and Ashok Agarwal. 2007. "Clinical Relevance of Oxidative Stress and Sperm Chromatin Damage in Male Infertility: an Evidence Based Analysis." International Braz J Urol: Official Journal of the Brazilian Society of Urology 33 (5) (September): 603-621.

de Mateo, Sara, Cristina Gázquez, Marta Guimerà, Juan Balasch, Marvin L Meistrich, José Luis Ballescà, and Rafael Oliva. 2009. "Protamine 2 Precursors (Pre-P2), Protamine 1 to Protamine 2 Ratio (P1/P2), and Assisted Reproduction Outcome." Fertility and Sterility 91 (3) (March): 715-722. doi:10.1016/j.fertnstert.2007.12.047.

de Mateo, Sara, Juan Martínez-Heredia, Josep Maria Estanyol, David Domínguez-Fandos, José Manuel Vidal-Taboada, José Luis Ballescà, and Rafael Oliva. 2007. "Marked Correlations in Protein Expression Identified by Proteomic Analysis of Human Spermatozoa." Proteomics 7 (23) (December): 4264-4277. doi:10.1002/pmic.200700521.

Eddy, Edward M, Kiyotaka Toshimori, and Deborah A O'Brien. 2003. "Fibrous Sheath of Mammalian Spermatozoa." Microscopy Research and Technique 61 (1) (May 1): 103-115. doi:10.1002/jemt.10320.

Gallo, J M, D Escalier, P Grellier, E Precigout, M Albert, G David, and J Schrevel. 1991. "Characterization of a Monoclonal Antibody to Human Proacrosin and Its Use in Acrosomal Status Evaluation." Journal of Histochemistry & Cytochemistry 39 (3) (March 1): 273-282. doi:10.1177/39.3.1704391.

Glander, H. J., J. Schiller, R. Süss, U. Paasch, S. Grunewald, and J. Arnhold. 2002. "Deterioration of Spermatozoal Plasma Membrane Is Associated with an Increase of Sperm Lyso-Phosphatidylcholines." Andrologia 34 (6): 360-366.

Kong, M, E S Diaz, and P Morales. 2009. "Participation of the Human Sperm Proteasome in the Capacitation Process and Its Regulation by Protein Kinase a and Tyrosine Kinase." Biology of Reproduction 80 (5) (April 28): 1026-1035. doi:10.1095/biolreprod.108.073924.

Krausz, Csilla. 2011. "Male Infertility: Pathogenesis and Clinical Diagnosis." Best Practice & Research Clinical Endocrinology & Metabolism 25 (2) (April 1): 271-285. doi:10.1016/j.beem.2010.08.006.

Liu, Rui-Zhi, Wan-Li Na, Hong-Guo Zhang, Zhi-Yong Lin, Bai-Gong Xue, and Zong-Ge Xu. 2008. "Assessment of Released Acrosin Activity as a Measurement of the Sperm Acrosome Reaction." Asian Journal of Andrology 10 (2) (March): 236-242. doi:10.1111/j.1745-7262.2008.00312.x.

Moretti, Elena, Giacomo Scapigliati, Nicola Antonio Pascarelli, Baccio Baccetti, and Giulia Collodel. 2007. "Localization of AKAP4 and Tubulin Proteins in Sperm with Reduced Motility." Asian Journal of Andrology 9 (5) (September): 641-649. doi:10.1111/j.1745-7262.2007.00267.x.

Nakamura, Noriko, Haruna Shibata, Deborah A O'Brien, Chisato Mori, and Edward M Eddy. 2008. "Spermatogenic Cell-Specific Type 1 Hexokinase Is the Predominant Hexokinase in Sperm." Molecular Reproduction and Development 75 (4) (April): 632-640. doi:10.1002/mrd.20791.

Oliva, R. 2006. "Protamines and Male Infertility." Human Reproduction Update 12 (4) (March 24): 417-435. doi:10.1093/humupd/dm1009.

Plessis, du, Stefan S, Anthony H Kashou, David J Benjamin, Satya P Yadav, and Ashok Agarwal. 2011. "Proteomics: a Subcellular Look at Spermatozoa." Reproductive Biology and Endocrinology 9 (1) (March 22): 36. doi:10.1186/1477-7827-9-36.

Rawe, V Y, E S Diaz, R Abdelmassih, C Wojcik, P Morales, P Sutovsky, and H E Chemes. 2008. "The Role of Sperm Proteasomes During Sperm Aster Formation and Early Zygote Development: Implications for Fertilization Failure in Humans." Human Reproduction (Oxford, England) 23 (3) (March 1): 573-580. doi:10.1093/humrep/dem385.

Sutovsky, P. 2011. "Sperm Proteasome and Fertilization." Reproduction (Cambridge, England) 142 (1) (July 13): 1-14. doi:10.1530/REP-11-0041.

Sutovsky, Peter. 2003. "Ubiquitin-Dependent Proteolysis in Mammalian Spermatogenesis, Fertilization, and Sperm Quality Control: Killing Three Birds with One Stone." Microscopy Research and Technique 61 (1) (May 1): 88-102. doi:10.1002/jemt.10319.

Thompson, W E. 2003. "Ubiquitination of Prohibitin in Mammalian Sperm Mitochondria: Possible Roles in the Regulation of Mitochondrial Inheritance and Sperm Quality Control." Biology of Reproduction 69 (1) (February 19): 254-260. doi:10.1095/biolreprod.102.010975.

Turner, R M, L R Johnson, L Haig-Ladewig, G L Gerton, and S B Moss. 1998. "An X-Linked Gene Encodes a Major Human Sperm Fibrous Sheath Protein, hAKAP82. Genomic Organization, Protein Kinase a-RII Binding, and Distribution of the Precursor in the Sperm Tail." The Journal of Biological Chemistry 273 (48) (November 27): 32135-32141.

Turner, R M, M P Musse, A Mandal, K Klotz, F C Jayes, J C Herr, G L Gerton, S B Moss, and H E Chemes. 2001. "Molecular Genetic Analysis of Two Human Sperm Fibrous Sheath Proteins, AKAP4 and AKAP3, in Men with Dysplasia of the Fibrous Sheath." Journal of Andrology 22 (2) (March): 302-315.

Wang, Mei-Jiao, Jia-Xian Ou, Guo-Wu Chen, Jun-Ping Wu, Hui-Juan Shi, Wai-Sum O, Patricia A Martin-DeLeon, and Hong Chen. 2012. "Does Prohibitin Expression Regulate Sperm Mitochondrial Membrane Potential, Sperm Motility, and Male Fertility?." Antioxidants & Redox Signaling 17 (3) (August): 513-519. doi:10.1089/ars.2012.4514.

World Health Organization. 2010. WHO Laboratory Manual for the Examination and Processing of Human Semen.

Xu, Wangjie, Hongliang Hu, Zhaoxia Wang, Xiaohui Chen, Fang Yang, Zijue Zhu, Peng Fang, et al. 2012. "Proteomic Characteristics of Spermatozoa in Normozoospermic Patients with Infertility." Journal of Proteomics 75 (17) (September 18): 5426-5436. doi:10.1016/j.jprot.2012.06.021.

Zahn, Astrid, Laura Ines Furlong, Juan Carlos Biancotti, Pablo Daniel Ghiringhelli, Clara Isabel Marijn-Briggiler, and Monica Hebe Vazquez-Levin. 2002. "Evaluation of the Proacrosin/Acrosin System and Its Mechanism of Activation in Human Sperm Extracts." Journal of Reproductive Immunology 54 (1-2) (March): 43-63.

Zimmerman, Shawn, and Peter Sutovsky. 2009. "The Sperm Proteasome During Sperm Capacitation and Fertilization." Journal of Reproductive Immunology 83 (1-2) (December): 19-25. doi:10.1016/j.jri.2009.07.006.

The invention claimed is:

1. A method for assessing sperm fertility rate in an infertile or hypofertile subject or a subject with difficulty to conceive for more than one year, comprising the steps of:
   i) liquefying a semen sample obtained from said subject at 37° C. for 30 minutes,
   ii) isolating spermatozoa from said semen sample through a single-step density gradient centrifugation,
   iii) washing said isolated spermatozoa with tris-buffered saline,
   iv) homogenizing said isolated spermatozoa with a lysis buffer to obtain a spermatozoa protein lysate,
   v) measuring the expression level of one or both of a kinase anchoring protein 4 (AKAP4) and Hexokinase 1 in said protein lysate, and
   vi) comparing said measured expression level with a reference value, wherein detecting a differential in the expression of the one or both of AKAP4 and Hexokinase 1 between the sample and the reference value is indicative of sperm fertility rate.

2. The method according to claim 1 wherein said subject is classified as a normozoospermic subject.

3. The method according to claim 1, wherein said tris-buffered saline comprises 0.1 mM of HCl, 100 mM of NaCl, and has a pH equal to 7.6.

4. The method according to claim 1, wherein step v) is performed by
   analyzing said spermatozoa protein lysate obtained in step iv) in a 1D SDS-PAGE with blue staining,
   providing a numerical analysis of said blue stained gel,
   selecting protein bands between Low molecular weights 15 to 30 kDA and protein bands between High molecular weights 80 and 110 kDa,
   representing each band by a densitometric curve and calculating the area under the densitometric curve, and
   calculating a ratio between the area under the densitometric curve from Low molecular weight and High molecular weight band intensities.

5. The method according to claim 4 wherein a ratio between 1 to 2 is indicative of good sperm quality, and a ratio above 2 is indicative of bad sperm quality.

6. The method according to claim 3, wherein step v) is performed by
   analyzing said spermatozoa protein lysate obtained in step iv) in a 1D SDS-PAGE with blue staining,
   providing a numerical analysis of said blue stained gel,
   selecting protein bands between Low molecular weights 15 to 30 kDA and protein bands between High molecular weights 80 and 110 kDa,
   representing each band by a densitometric curve and calculating the area under the densitometric curve, and
   calculating a ratio between the area under the densitometric curve from Low molecular weight and High molecular weight band intensities.

7. A method enabling an infertile or hypofertile subject or a subject with difficulty to conceive for more than one year to determine the most successful assisted-reproductive technology comprising the steps of:
   i) liquefying a semen sample obtained from said subject at 37° C. for 30 minutes,
   ii) isolating spermatozoa from said semen sample through a single-step density gradient centrifugation,
   iii) washing said isolated spermatozoa with tris-buffered saline,
   iv) homogenizing said isolated spermatozoa with a lysis buffer to obtain a spermatozoa protein lysate,
   v) measuring the expression level of one or both of AKAP4 and Hexokinase 1 in said protein lysate, and
   vi) comparing said measured expression level with a reference value, wherein detecting a differential in the expression of the one or both of AKAP4 and Hexokinase 1 between the sample and the reference value is indicative of a given assisted reproductive technology.

8. The method according to claim 7, wherein step v) is performed by
   analyzing said spermatozoa protein lysate obtained in step iv) in a 1D SDS-PAGE with blue staining,
   providing a numerical analysis of said blue stained gel,
   selecting protein bands between Low molecular weights 15 to 30 kDA and protein bands between High molecular weights 80 and 110 kDa,
   representing each band by a densitometric curve and calculating the area under the densitometric curve, and
   calculating a ratio between the area under the densitometric curve from Low molecular weight and High molecular weight band intensities,
wherein when said ratio is above 2 choosing intrauterine insemination (IUI) as an assisted-reproductive technology.

9. The method according to claim 7, wherein said tris-buffered saline comprises 0.1 mM of HCl, 100 mM of NaCl and has a pH equal to 7.6.

10. The method according to claim 7, wherein said subject is classified as a normozoospermic subject.

* * * * *